(12) United States Patent
Yang et al.

(10) Patent No.: US 9,459,964 B2
(45) Date of Patent: Oct. 4, 2016

(54) METHOD AND APPARATUS FOR PROCESSING ERROR EVENT OF MEDICAL DIAGNOSIS DEVICE, AND FOR PROVIDING MEDICAL INFORMATION

(71) Applicant: SAMSUNG ELECTRONICS CO., LTD., Suwon-si (KR)

(72) Inventors: Dong-jin Yang, Seoul (KR); Nasir Desai, Suwon-si (KR); Rakesh Dutta, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 133 days.

(21) Appl. No.: 14/444,003

(22) Filed: Jul. 28, 2014

(65) Prior Publication Data

US 2015/0033073 A1   Jan. 29, 2015

(30) Foreign Application Priority Data

Jul. 26, 2013   (KR) .................. 10-2013-0088983

(51) Int. Cl.
*G06F 11/00* (2006.01)
*G06F 11/14* (2006.01)
*A61B 5/00* (2006.01)

(52) U.S. Cl.
CPC ......... *G06F 11/1438* (2013.01); *A61B 5/0022* (2013.01); *A61B 5/743* (2013.01); *A61B 5/7405* (2013.01); *G06F 11/1446* (2013.01); *A61B 2560/0276* (2013.01)

(58) Field of Classification Search
CPC .................... G06F 11/1438; G06F 11/1446
USPC .................... 714/37, 15, 36, 39, 47.1, 48
See application file for complete search history.

(56) References Cited

U.S. PATENT DOCUMENTS 7,240,251 B2 * 7/2007 Popescu .................. H05G 1/54
378/21
2003/0195399 A1   10/2003 Phipps
(Continued)

FOREIGN PATENT DOCUMENTS

JP   2007-252415 A   10/2007
JP   2008-123150 A   5/2008
(Continued)

OTHER PUBLICATIONS

Communication dated Oct. 17, 2014 issued by Korean Intellectual Property Office in counterpart Korean Patent Application No. 10-2013-0088983.
(Continued)

*Primary Examiner* — Dieu-Minh Le
(74) *Attorney, Agent, or Firm* — Sughrue Mion, PLLC

(57) ABSTRACT

A method and an apparatus for processing an error event of a medical diagnosis device is provided that includes detecting an error event at a medical diagnosis system, determining an error correcting mode from among a first mode for restarting a diagnosis process at which the error event occurred, a second mode for informing the error event to components of the medical diagnosis system at which the error event did not occur, and a third mode for stopping operation of the medical diagnosis system, based on information regarding the error event, and processing the error event based on the determined error correcting mode. There is also provided a method for providing medical information that includes receiving medical data, providing a diagnosis process a first region, providing log data at a second region, and providing video data at a third region of the screen image.

39 Claims, 10 Drawing Sheets

(56) References Cited

U.S. PATENT DOCUMENTS

| | | |
|---|---|---|
| 2003/0216625 A1 | 11/2003 | Phipps |
| 2008/0189075 A1* | 8/2008 | Rodriquez .............. G06F 11/30 702/183 |
| 2010/0046818 A1 | 2/2010 | Yamaya et al. |

FOREIGN PATENT DOCUMENTS

| | | |
|---|---|---|
| JP | 2009-233177 A | 10/2009 |
| JP | 2010-033116 A | 2/2010 |
| JP | 2011-36560 A | 2/2011 |
| KR | 10-0132950 B1 | 4/1998 |
| KR | 10-2008-0029066 A | 4/2008 |
| KR | 10-2009-0132893 A | 12/2009 |
| KR | 10-2010-0072515 A | 7/2010 |

OTHER PUBLICATIONS

Communication dated Oct. 20, 2014 issued by International Searching Authority in counterpart International Patent Application No. PCT/KR2014/006781.

* cited by examiner

METHOD AND APPARATUS FOR PROCESSING ERROR EVENT OF MEDICAL DIAGNOSIS DEVICE, AND FOR PROVIDING MEDICAL INFORMATION

CROSS-REFERENCE TO RELATED PATENT APPLICATION

This application claims priority from Korean Patent Application No. 10-2013-0088983, filed on Jul. 26, 2013, in the Korean Intellectual Property Office, the disclosure of which is incorporated herein by reference in its entirety.

BACKGROUND

1. Technical Field

Apparatuses and methods consistent with exemplary embodiments relate to a method and an apparatus for processing an error event of a medical diagnosis device, and for providing medical information to a user.

2. Description of the Related Art

A medical diagnosis device may include a large number of parts and components for processing clinical information and diagnosing a target object. Accordingly, a user operating the medical diagnosis device may require thorough experience and understanding of the medical diagnosis device and its many parts and components in order to operate the device.

In addition to maloperation of a medical diagnosis device by a user, errors may occur during operation of a medical diagnosis device due to hardware/software issues of the medical diagnosis device. In other words, operation of a medical diagnosis device may be interrupted, or performance of the medical diagnosis device may be deteriorated, due to unexpected issues.

In the related art, to resolve such issues, log information stored in a console device of a medical diagnosis device is analyzed and/or a debugging process using a debugging board is performed.

SUMMARY

Exemplary embodiments address at least the above problems and/or disadvantages and other disadvantages not described above. Also, the exemplary embodiments are not required to overcome the disadvantages described above, and may not overcome any of the problems described above.

According an aspect of an exemplary embodiment, there is provided a method for processing an error event using an error monitoring device, the method including detecting an error event at a medical diagnosis system, determining an error correcting mode from among a first mode for restarting a diagnosis process at which the error event occurred, a second mode for informing the error event to components of the medical diagnosis system at which the error event did not occur, and a third mode for stopping operation of the medical diagnosis system, based on information regarding the error event, and processing the error event based on the determined error correcting mode.

The detecting of the error event may include receiving information regarding the diagnosis process at which the error event occurred.

The second mode, information regarding the diagnosis process may be transmitted to components at which the error event did not occur.

The determining of the error correcting mode may include determining the error correcting mode based on a time point at which the error event is detected.

The determining of the error correcting mode may further include determining the error correcting mode based on a sector of the overall diagnosis processes that corresponds to the diagnosis process at which the error event occurred.

The method may further include transmitting the error event to a medical data managing device.

The determining of the error correcting mode may include determining the error correcting mode based on an error correcting signal received from a medical data providing device, wherein the medical data managing device informs the medical data providing device of the error event.

According to an aspect of another exemplary embodiment, there is provided an error monitoring device configured to process an error event, the error monitoring device including an error detector configured to detect an error event at a medical diagnosis system, a mode determiner configured to determine an error correcting mode from among a first mode for restarting a diagnosis process at which the error event occurred, a second mode for informing the error event to components of the medical diagnosis system at which the error event did not occur, and a third mode for stopping operation of the medical diagnosis system, based on information regarding the error event, and an error resolving unit configured to process the error event based on the determined error correcting mode.

The error detector may be further configured to receive information regarding the diagnosis process at which the error event occurred.

In the second mode, information regarding the diagnosis process may be transmitted to components at which the error event did not occur.

The mode determiner may be further configured to determine the error correcting mode based on a time point at which the error event is detected.

The mode determiner may be further configured to determine the error correcting mode based on a sector of the overall diagnosis processes that corresponds to the diagnosis process at which the error event occurred.

The error monitoring device may further include a communication unit configured to transmit the error event to a medical data managing device.

The mode determiner may be further configured to determine the error correcting mode based on an error correcting signal received from a medical data providing device, and wherein the medical data managing device may be configured to inform the medical data providing device of the error event.

According to an aspect of another exemplary embodiment, there is provided a method for providing medical information using a medical data providing device, the method including receiving medical data from a medical data managing device, providing a diagnosis process related to the medical data at a first region of a screen image, providing log data from the medical data that corresponds to the diagnosis process at a second region of the screen image based on a user input for selecting the diagnosis process from among a plurality of diagnosis processes, and providing video data from the medical data that corresponds to the selected diagnosis process at a third region of the screen image.

The medical data may relate to an error event at a medical diagnosis system.

The medical data may relate to predetermined periods of time before and after a time point at which the error event occurred.

The providing of the diagnosis process may include displaying the diagnosis process at which the error event is detected to be visually distinguishable.

The providing of the log data may include displaying log data corresponding to the detection of the error event to be visually distinguishable.

The providing of the video data may include displaying video data corresponding to the detection of the error event to be visually distinguishable.

The log data may provide at the second region and the video data provided at the third region are synchronized with each other.

The providing of the diagnosis process may include assorting and displaying a plurality of diagnosis processes in an order in which the plurality of diagnosis processes are carried out.

The second region may be adjacent to the first region at which the selected diagnosis process is displayed.

The video data may include at least one of video data showing a gantry, video data showing a user input unit, video data showing recorded screen images of a console unit, video data showing a target object, video data showing an interior of a shielded room, and video data showing diagnosis of the target object.

The medical data may further include voice data.

According to an aspect of another exemplary embodiment, there is provided a medical data providing device for providing medical data, the medical data managing device including a communication unit configured to receive medical data from a medical data managing device, and a display configured to provide a diagnosis process related to the medical data at a first region of a screen image, provide log data from the medical data that corresponds to the diagnosis process at a second region of the screen image based on a user input for selecting the diagnosis process from among a plurality of diagnosis processes, and providing video data from the medical data that corresponds to the selected diagnosis process at a third region of the screen image.

The medical data may relate to an error event at a medical diagnosis system.

The medical data may relate to predetermined periods of time before and after a time point at which the error event occurred.

The display may be further configured to display the diagnosis process at which the error event is detected to be visually distinguishable.

The display may be further configured to display log data corresponding to the detection of the error event to be visually distinguishable.

The display may be further configured to display video data corresponding to the detection of the error event to be visually distinguishable.

The log data provided at the second region and the video data provided at the third region may be synchronized with each other.

The display may be further configured to assort and display a plurality of diagnosis processes in an order in which the plurality of diagnosis processes are carried out.

The second region may be adjacent to the first region at which the selected diagnosis process is displayed.

The video data may include at least one of video data showing a gantry, video data showing a user input unit, video data showing recorded screen images of a console unit, video data showing a target object, video data showing an interior of a shielded room, and video data showing diagnosis of the target object.

The medical data may further include voice data. According to another aspect of the present invention, there is provided a computer readable recording medium having recorded thereon a computer program for implementing the method an error monitoring device processes an error event.

According to another aspect of the present invention, there is provided a computer readable recording medium having recorded thereon a computer program for implementing the method that a medical data providing device provides medical information.

BRIEF DESCRIPTION OF THE DRAWINGS

The above and/or other aspects will become apparent and more readily appreciated from the following description of exemplary embodiments taken in conjunction with the accompanying drawings, in which.

DETAILED DESCRIPTION

Figure 1:
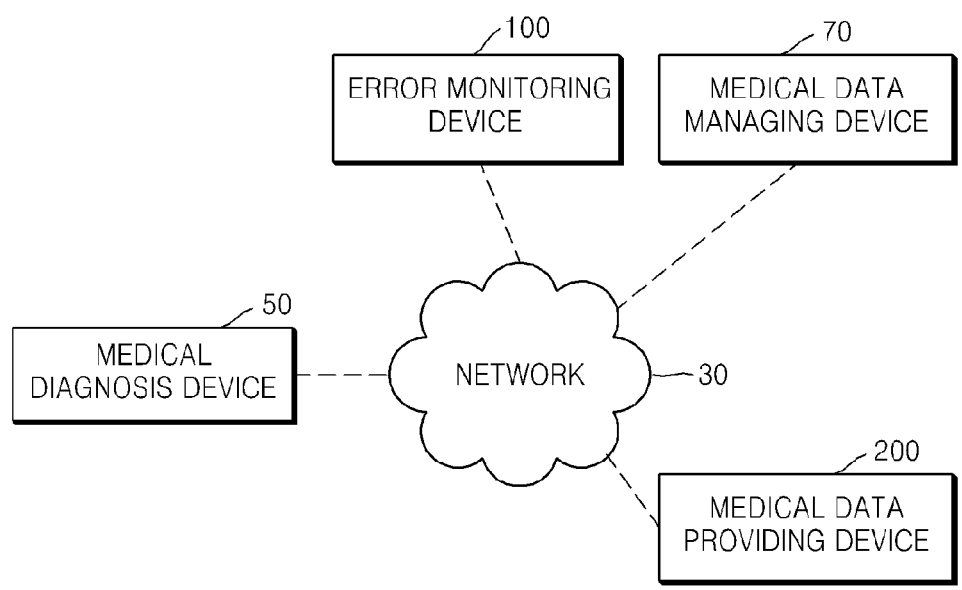
FIG. 1 is a diagram showing a medical diagnosis system according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

Although the terms used in one or more exemplary embodiments are selected from generally known and used terms, some of the terms mentioned in the description have been selected by the applicant at his or her discretion, the detailed meanings of which are described in relevant parts of the description herein.

In addition, unless explicitly described to the contrary, the word "comprise" and variations such as "comprises" or "comprising" will be understood to imply the inclusion of stated elements but not the exclusion of any other elements. In addition, the term "units" described in the specification mean units for processing at least one function and operation and can be implemented by software components or hardware components, such as FPGA or ASIC. However, the "units" are not limited to software components or hardware components. The "units" may be embodied on a recording medium and may be configured to operate one or more processors.

Therefore, for example, the "units" may include components, such as software components, object-oriented software components, class components, and task components, processes, functions, properties, procedures, subroutines, program code segments, drivers, firmware, micro codes, circuits, data, databases, data structures, tables, arrays, and variables. Components and functions provided in the "units" may be combined to smaller numbers of components and "units" or may be further divided into larger numbers of components and "units."

The term "image" or "video" may refer to multi-dimensional data consisting of discrete image elements (e.g., pixels in a 2D image and voxels in a 3D image). For example, images may include a medical image regarding a target object obtained via X-ray, CT, MRI, ultrasonography, and other medical diagnosis devices.

Furthermore, the term "target object" or "examinee" may refer to a human, an animal, or a portion of a human or an animal. For example, the target object may include an organ, such as a liver, a heart, a uterus, a brain, a breast, or a stomach, or a blood vessel. Furthermore, the term "target object" or the "examinee" may include a phantom. A phantom refers to a material having a volume that is very similar to density and effective atomic number of a living thing and may include a spherical phantom having properties similar to those of a human body.

Furthermore, the term "user" may refer to a medical expert, which may be a doctor, a nurse, a medical technologist, a medical imaging expert, a radiological technologist, or a medical device repairman, but is not limited thereto.

Hereinafter, exemplary embodiments will be described in detail with reference to the accompanying drawings. Various changes and numerous exemplary embodiments as allowed and particular exemplary embodiments will be illustrated in the drawings and described in detail in the written description. However, this is not intended to limit one to particular modes of practice, and it is to be appreciated that all changes, equivalents, and substitutes that do not depart from the spirit and technical scope are encompassed in one or more exemplary embodiments. Those components that are the same or are in correspondence are rendered the same reference numeral regardless of the figure number, and redundant explanations are omitted. In the description, certain detailed explanations of related art are omitted when it is deemed that they may unnecessarily obscure one or more exemplary embodiments.

FIG. 1 is a diagram showing a medical diagnosis system according to an exemplary embodiment.

The medical diagnosis system according to the present exemplary embodiment includes a medical diagnosis device 50, an error monitoring device 100, a medical data managing device 70, and a medical data providing device 200. One or more components included in the medical diagnosis system may be mutually connected wirelessly or with wires via a network 30.

First, the medical diagnosis device 50 refers to a device that performs medical diagnosis regarding a target object. The medical diagnosis device 50 may generate a medical image regarding a target object located at a gantry according to a predetermined protocol, sequence, or pattern.

The medical diagnosis device 50 according to an exemplary embodiment may include a console unit which controls and manages the medical diagnosis device 50 and receives user inputs, a sequence controller which controls medical-purpose signals transmitted to a target object, a gantry controller which controls a gantry at which a target object is located, an image reconstructing unit which generates a medical image regarding a target object, and the gantry on which a target object is located. The configurations described above are merely examples. The medical diagnosis device 50 may further include components other than the components described above or may include fewer components than the components described above.

The medical diagnosis device 50 according to an exemplary embodiment may include at least one from among a magnetic resonance imaging (MRI) diagnosis device, an X-ray diagnosis device, a computer tomography (CT) diagnosis device, and an ultrasonography diagnosis device. However, the diagnosis devices stated above are merely examples, and the medical diagnosis device 50 may include any of various diagnosis devices with modality other than the diagnosis devices stated above, The error monitoring device 100 monitors the medical diagnosis device 50 and determines whether an error occurs at the medical diagnosis device 50. In other words, the error monitoring device 100 may detect an error event occurring at the medical diagnosis device 50. Furthermore, the error monitoring device 100 may process an error event.

The term "error event" may refer to an unexpected effect to the medical diagnosis device 50 due to maloperation of the medical diagnosis device 50 by a user, software or hardware errors, or movement of a target object.

For example, operation of the medical diagnosis device 50 may be urgently interrupted due to maloperation of a user. Alternatively, it may be impossible for the medical diagnosis device 50 to operate normally due to failures or crashes of hardware or software. Alternatively, diagnosis may be interrupted due to unintended movement of a target object. Furthermore, some or all of functions of the medical diagnosis device 50 may be interrupted due to wear-off of components, temperature rise due to damages to a cooling fan, abnormal power supply, or malfunction in circuits. In other words, the term "error event" may refer to any unexpected results occurred at the medical diagnosis device 50 other than those in the above exemplary embodiments. The error monitoring device 100 may monitor error events occurring at the medical diagnosis device 50.

Furthermore, the error monitoring device 100 may inform an error event occurring at the medical diagnosis device 50 to the medical data managing device 70. Detailed descriptions of the error monitoring device 100 will be described below with reference to FIGS. 2 and 3.

The medical data managing device 70 collects and manages medical data. The term "medical data" may refer to data obtained by the medical data managing device 70 in relation to error events, where medical data according to an exemplary embodiment may include video data and log data. Medical data may further include various types of data other than video data and log data, e.g., voice data.

The term "log data" may refer to system information of the medical diagnosis device 50. In other words, the medical data managing device 70 may receive and store system information of the medical diagnosis device 50 collected by a console unit of the medical diagnosis device 50 and manages the system information as log data. Log data according to an exemplary embodiment may include information regarding a time point at which system data is generated or modified, and may also include information regarding processes currently being performed at a time point at which an error event occurs at the medical diagnosis device 50.

The term "video data" may refer to various types of video images related to the medical diagnosis device 50, and may include both a still image and a moving picture. For example, video data may include data obtained by capturing various visually recognizable data including data obtained by capturing an image nearby a gantry of the medical diagnosis device 50, data obtained by capturing an image of a console unit or a user input unit of the medical diagnosis device 50, data obtained by recording screen images output to the console unit of the medical diagnosis device 50, data obtained by capturing an image of a target object located at the gantry, data obtained by capturing an image inside a shielded room, and medical image data that is a result of diagnosis regarding the target object.

The medical data managing device 70 collects and manages the medical data as described above, where various data included in the medical data, such as log data, video data, and voice data, may be synchronized with one another and stored.

The medical data providing device 200 receives medical data from the medical data managing device 70 and provides the medical data to a user. The medical data providing device 200 may provide medical data to a user by visually and acoustically outputting the received log data, video data, and voice data. The medical data providing device 200 according to an exemplary embodiment may be a device of a service center or a control center regarding the medical diagnosis device 50.

The medical data providing device 200 may synchronize various types of medical data and output the synchronized medical data, such that a user may easily analyze an error event at the medical diagnosis device 50. The medical data providing device 200 according to another exemplary embodiment may apply visual effects, such that a portion of medical data provided to a user is distinguished from the remaining portion of the medical data. Furthermore, the medical data providing device 200 may output not only medical data, but also a list of a plurality of diagnosis processes regarding a target object. Detailed descriptions thereof will be given below with reference to FIGS. 10 through 12.

In the medical diagnosis system described above, the error monitoring device 100 detects and processes an error event at the medical diagnosis device 50 and informs the error event to the medical data managing device 70. The medical data providing device 200 provides medical data received from the medical data managing device 70 to a user of the medical data providing device 200, such that the user may easily analyze the error event.

Figure 2:
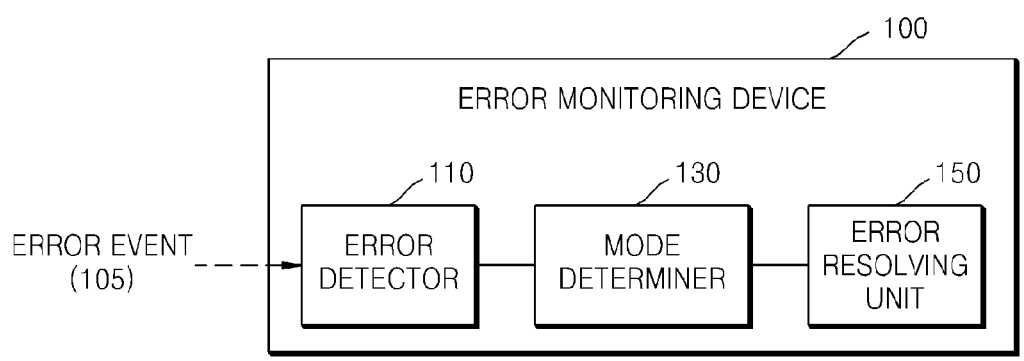
FIG. 2 is a block diagram showing the configuration of an error monitoring device according to an exemplary embodiment.

FIG. 2 is a block diagram showing the configuration of the error monitoring device 100 according to an exemplary embodiment. The error monitoring device 100 according to an exemplary embodiment may include an error detector 110, a mode determiner 130, and an error processor 150. However, one or more exemplary embodiments are not limited thereto, and the error monitoring device 100 may include more components or fewer components than the above-stated components.

The error detector 110 detects an error event 105 occurring at the medical diagnosis device 50. As described above, the error event 105 may refer to any unexpected results due to various issues including hardware or software issue of the medical diagnosis device 50, a user's maloperation, movement of a target object, etc.

The error event 105 may be detected by one or more components included in the medical diagnosis device 50. In other words, the error detector 110 periodically collects information regarding current states of a plurality of components included in the medical diagnosis device 50 and information regarding processes currently being performed. The error detector 110 according to an exemplary embodiment may exchange data with the medical diagnosis device 50 through wired connection or wirelessly according to the TCP/IP protocol.

Next, when the error processor 150 occurs at one or more components of the medical diagnosis device 50, the error detector 110 detects the error event 105 occurring at the medical diagnosis device 50. In other words, the error detector 110 may detect the error event 105 by receiving a signal indicating occurrence of the error event 105 from components of the medical diagnosis device 50.

As the error event 105 occurs, the error detector 110 may receive information regarding a diagnosis process at which the error event 105 occurred. In other words, the medical diagnosis device 50 diagnoses a target object via a plurality of diagnosis processes, and the error event 105 may occur at one from among the diagnosis processes during the diagnosis. Therefore, the error detector 110 may receive information indicating a particular time point at which the error event 105 occurs during the entire process, together with information regarding occurrence of the error event 105. Detailed descriptions thereof will be given below with reference to FIG. 6.

The mode determiner 130 determines an error correcting mode. The mode determiner 130 may determine an error correcting mode for processing the error event 105 by using information regarding the error event 105 that is recognized by the error detector 110. The term "error correcting mode" refers by which the error monitoring device 100 controls the medical diagnosis device 50 to process the error event 105 and may include at least one from among a first mode, a second mode, and a third mode that are described below. Detailed descriptions of the error correcting mode will be given below together with that of the error processor 150.

The mode determiner 130 according to an exemplary embodiment may determine an error correcting mode based on a time point at which the error processor 150 is detected. In other words, as described above, the error detector 110 receives information regarding a diagnosis process at which the error event 105 occurred from the medical diagnosis device 50, and the mode determiner 130 may determine an error correcting mode based on the received information regarding the diagnosis process.

In detail, the mode determiner 130 may analyze to which sector of the overall diagnosis processes the diagnosis process corresponding to the time point of the error event 105 belongs and determine an error correcting mode based on a result of the analysis. Detailed descriptions thereof will be given below with reference to FIG. 6.

The error processor 150 processes the error event 105 according to the error correcting mode determined by the mode determiner 130. In other words, if the mode determiner 130 determines at least one from among a first mode, a second mode, and a third mode as an error correcting mode, the error processor 150 may control the medical diagnosis device 50 according to the determined error correcting mode and process the error event 105. Detailed descriptions of the error correcting mode will be given below.

According to the first mode from among the error correcting modes, the error processor 150 controls the medical diagnosis device 50 to restart a diagnosis process at which the error event 105 is detected. The error processor 150 may control the medical diagnosis device 50 to restart a diagnosis process that is terminated or is in standby as the error event 105 occurs. In other words, if the error event 105 is an insignificant error and has no or little effect to a target object, the medical diagnosis device 50 may simply restart the corresponding diagnosis process.

For example, if a target object located at a gantry moves before an imaging operation regarding the target object starts, effect to the overall diagnosis processes is little. Therefore, a user of the medical diagnosis device 50 may instruct the target object to not to move. According to the present exemplary embodiment, if a diagnosis process at which the error event 105 occurs is before initiation of an imaging operation, the mode determiner 130 may determine the first mode as the error correcting mode.

The error processor 150 may control the medical diagnosis device 50 in the first mode and restart an imaging preparation process. In other words, the error processor 150 may control the medical diagnosis device 50 to keep restarting an imaging preparation process without starting an imaging operation until the error event 105 is processed.

According to the second mode from among the error correcting modes, the error processor 150 controls the medical diagnosis device 50 to inform the error event 105 to components at which the error event 105 did not occur. In other words, if the error event 105 occurs at one or more of a plurality of components included in the medical diagnosis device 50, the error processor 150 may inform the error event 105 to other components of the medical diagnosis device 50, such that information regarding the error event 105 is shared within the medical diagnosis device 50.

For example, the error event 105 may occur at a sequence controller, which is one from among components included in the medical diagnosis device 50, during a process for selecting a protocol or a sequence. As the error event 105 occurs during a sequence selecting process, the mode determiner 130 may determine the second mode as the error correcting mode.

The error processor 150 may control the medical diagnosis device 50 to inform the error event 105 in the second mode. In other words, the error processor 150 may transmit information informing occurrence of the error event 105 to components at which the error event 105 did not occur, such as a console unit, a gantry controller, an image reconstructing unit, and a gantry. Therefore, the entire components may share information regarding progress of the overall diagnosis processes.

When the error processor 150 according to an exemplary embodiment informs the error event 105 in the second mode, the error processor 150 may also transmit information regarding a diagnosis process at which the error event 105 occurred. In other words, the error processor 150 may not only inform about occurrence of the error event 105, but also inform about a particular diagnosis process at which the error event 105 occurred.

According to the third mode from among the error correcting modes, the error processor 150 may control the medical diagnosis device 50 to stop operation of the medical diagnosis device 50. In other words, if the error event 105 is a serious error occurred during an imaging operation regarding a target object, the mode determiner 130 may determine the third mode as the error correcting mode.

Next, to minimize effects inflicted by the error event 105 to the target object, the error processor 150 may stop operation of the medical diagnosis device 50. Therefore, the medical diagnosis device 50 may stop diagnosis processes in progress and stand by until the error event 105 is processed.

The mode determiner 130 may select one or more from among the first mode, the second mode, and the third mode as error correcting modes, rather than selecting one from among the first mode, the second mode, and the third mode as the error correcting mode. In other words, if the mode determiner 130 determines the first mode and the second mode as the error correcting modes, the error processor 150 may restart a diagnosis process at which the error event 105 is detected and informs about the error event 105 to other components of the medical diagnosis device 50. In the same regard, if the second mode and the third mode are the error correcting modes, the error processor 150 may stop operation of the medical diagnosis device 50 and inform about the error event 105.

The error monitoring device 100 including the above-stated components may detect and process error events occurring at the medical diagnosis device 50. Therefore, before a user performs an ex post facto analysis regarding an error event, the error event may be processed in various error correcting modes.

Figure 3:
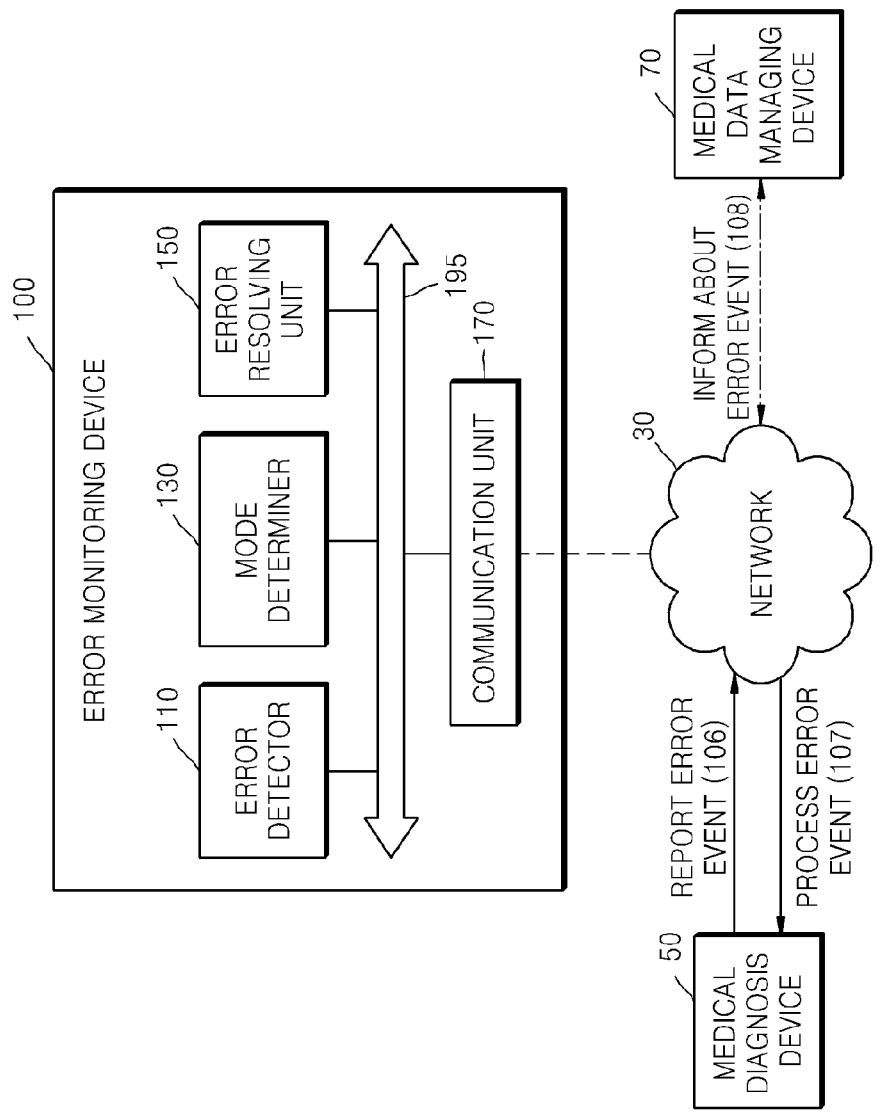
FIG. 3 is a block diagram showing the configuration of an error monitoring device according to another exemplary embodiment.

FIG. 3 is a block diagram showing the configuration of the error monitoring device 100 according to another exemplary embodiment. The error monitoring device 100 according to the exemplary embodiment shown in FIG. 3 may further include a communication unit 170. Descriptions of components identical to those shown in FIG. 2 will be omitted below.

The communication unit 170 is connected to the network 30 through a wired connection or wirelessly and communicates with an external device or a server. The communication unit 170 may exchange data with a hospital server connected via a picture archiving and communication system (PACS), an external server, the medical diagnosis device 50, the medical data managing device 70, and the medical data providing device 200. Furthermore, the communication unit 170 may perform data communication according to the digital imaging and communication in medicine (DICOM) standard or the TCP/IP protocol.

The communication unit 170 may receive information regarding an error event via the network 30 (an operation 106), and may also transmit an error event processing order for controlling the medical diagnosis device 50 (an operation 107). Furthermore, the communication unit 170 may inform about an error event occurred at the medical diagnosis device 50 to the medical data managing device 70 (an operation 108).

For another example, according to another exemplary embodiment, the communication unit 170 may receive an error correction signal from the medical data providing device 200. In other words, the communication unit 170 may receive an error correction signal for determining an error correcting mode from the medical data providing device 200, and thus the mode determiner 130 may select an error correcting mode based on the error correction signal.

The components of the error monitoring device 100 including the communication unit 170 may be connected to one another via a system bus 195. Furthermore, the communication unit 170 may include one or more components that enable communication via the network 30, e.g., a close-distance communication module and a wired communication module.

The term close-distance communication module refers to a module for close-distance communication within a predetermined distance. Examples of the close-distance communication techniques according to an exemplary embodiment may include wireless LAN, Wi-Fi, Bluetooth, Zigbee, Wi-Fi Direct (WFD), ultra wideband (UWB), infrared data association (IrDA), Bluetooth Low Energy (BLE), and near field communication (NFC). However, one or more exemplary embodiments are not limited thereto.

The term wired communication module refers to a module for communication using electric signals or optical signals. Examples of the wired communication techniques according to an exemplary embodiment may include a pair cable, a coaxial cable, an optical fiber cable, and an Ethernet cable.

Hereinafter, a method of processing an error event using components included in the error monitoring device 100 will be described with reference to FIGS. 4 and 5. The flowcharts shown in FIGS. 4 and 5 include operations that are chronologically carried out by the error monitoring device 100, the error detector 110, the mode determiner 130, the error processor 150, and the communication unit 170 shown in FIGS. 2 and 3. Therefore, even if omitted below, any of descriptions given above in relation to the components shown in FIGS. 2 and 3 also apply to the flowcharts shown in FIGS. 4 and 5.

Figure 4:
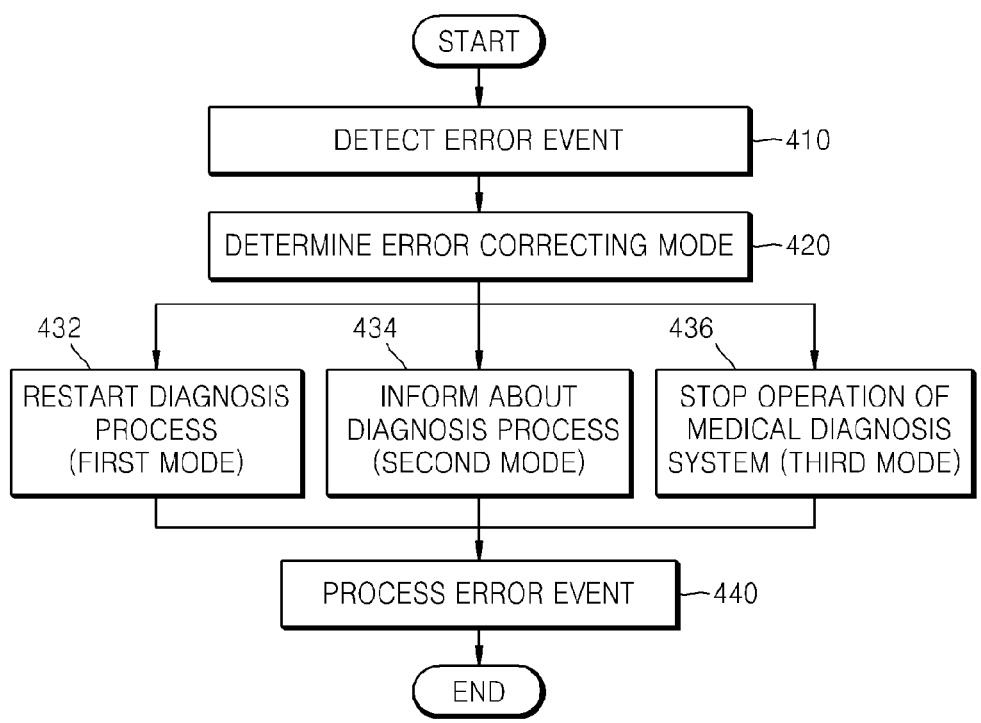
FIG. 4 is a flowchart showing a method of processing an error event according to an exemplary embodiment.

FIG. 4 is a flowchart showing a method of processing an error event according to an exemplary embodiment.

In an operation 410, the error monitoring device 100 detects an error event occurring at the medical diagnosis device 50. In other words, the error monitoring device 100 receives information regarding error events occurring at some or all of a plurality of components included in the medical diagnosis device 50. The error monitoring device 100 may also acquire information regarding a diagnosis process at which the corresponding error event occurred, together with the information regarding the error event.

In an operation 420, the error monitoring device 100 determines an error correcting mode based on the information regarding the error event. The error monitoring device 100 may determine at least one from among the first mode, the second mode, and the third mode as described above as the error correcting mode. The error monitoring device 100 may determine the error correcting mode based on a sector of the overall diagnosis processes the corresponding diagnosis process at which the error event occurred belongs.

In an operation 432, the error monitoring device 100 determines the first mode for restarting a diagnosis process at which an error event occurred as the error correcting mode. Next, in an operation 440, the error monitoring device 100 may control the medical diagnosis device 50 in the first mode and process the error event.

In an operation 434, the error monitoring device 100 determines the second mode for informing about an error event as the error correcting mode. Next, in an operation 440, the error monitoring device 100 may control the medical diagnosis device 50 in the second mode and process the error event. In other words, the error monitoring device 100 may restart a diagnosis process that is interrupted or is in standby as an error event is detected, in the first mode.

In other words, the error monitoring device 100 may transmit information regarding the error event to components included in the medical diagnosis device 50 other than the component at which the error event occurred in the operation 440. The error monitoring device 100 may also transmit information regarding a diagnosis process at which the error event occurred, together with the information indicating occurrence of the error event.

In an operation 436, the error monitoring device 100 determines the third mode for stopping operation of the medical diagnosis device 50 as the error correcting mode. Next, in the operation 440, the error monitoring device 100 may control the medical diagnosis device 50 in the third mode and process the error event. In other words, if an error event occurs at a diagnosis process which seriously affects a target object or the overall components of the medical diagnosis device 50, the error monitoring device 100 may determine the third mode as the error correcting mode and stop operation of the medical diagnosis device 50.

As described above, the error monitoring device 100 may determine either one from among the first mode, the second mode, and the third mode as the error correcting mode or two or more from among the first mode, the second mode, and the third mode as the error correcting mode to process an error event.

Furthermore, according to another exemplary embodiment, the error monitoring device 100 may transmit information regarding occurrence of an error event to the medical data managing device 70 after the operation 440. Therefore, the medical data managing device 70 may collect medical data before and after the time point at which the error event occurred and transmit the medical data to the medical data providing device 200.

Figure 5:
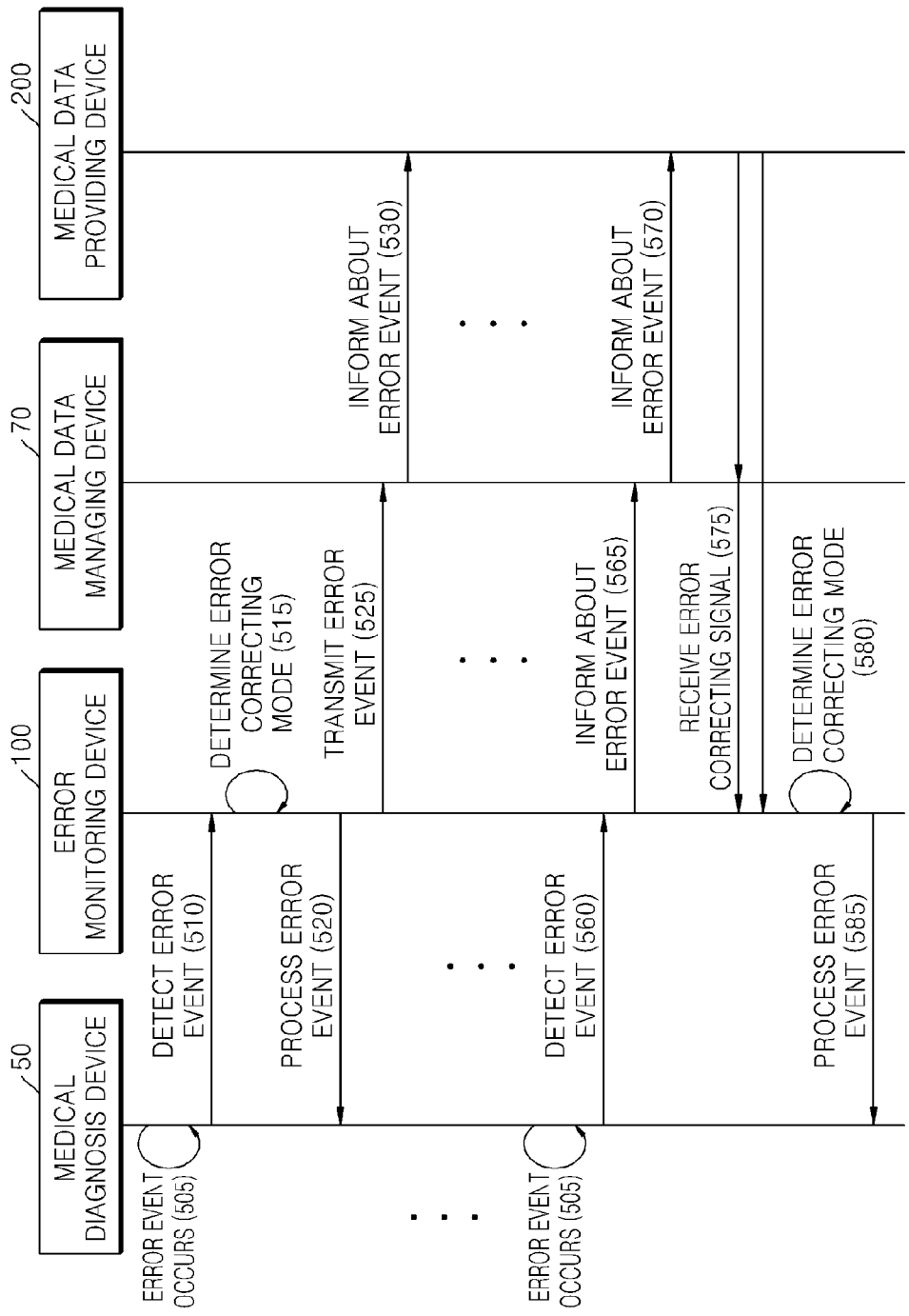
FIG. 5 is a flowchart showing a method of processing an error event according to an exemplary embodiment.

FIG. 5 is a flowchart showing a method of processing an error event according to an exemplary embodiment. Descriptions already given above with reference to FIG. 4 will be omitted below.

In an operation 505, an error event occurs at the medical diagnosis device 50. In other words, error events may occur at some or all of components included in the medical diagnosis device 50.

In an operation 510, the error monitoring device 100 detects an error event of the medical diagnosis device 50. When occurrence of an error event is detected, the error monitoring device 100 may obtain information regarding a diagnosis process at which the error event occurred.

In an operation 515, the error monitoring device 100 determines an error correcting mode based on information regarding the error event. The error correcting mode may include at least one from among the first mode, the second mode, and the third mode. Next, in an operation 520, the error monitoring device 100 controls the medical diagnosis device 50 in the determined error correcting mode and process the error event.

In an operation 525, the error monitoring device 100 informs about the error event to the medical data managing device 70. In an operation 530, the medical data managing device 70 may transmit medical data related to the error event from among medical data, which are obtained as the error event is informed, to the medical data providing device 200. As described above with reference to FIG. 1, the medical data may include log data, video data, and voice data.

In an operation 555, a new error event occurs at the medical diagnosis device 50. In other words, in the operation 555, an error event different from the error event processed by the error monitoring device 100 in the operation 520 occurs. In an operation 560, the error monitoring device 100 detects the new error event at the medical diagnosis device 50.

In an operation 565, the error monitoring device 100 informs about the error event to the medical data managing device 70. In other words, before an error correcting mode is determined, the error monitoring device 100 may inform occurrence of the new error event to the medical data managing device 70. In an operation 570, the medical data managing device 70 informs about the new error event to the medical data providing device 200 as in the operation 530.

In an operation 575, the error monitoring device 100 receives an error correction signal from the medical data providing device 200. The error correction signal may be transmitted from the medical data providing device 200 to the error monitoring device 100 via the medical data managing device 70 as shown in FIG. 5 or may be transmitted directly from the medical data providing device 200 to the error monitoring device 100.

In an operation 580, the error monitoring device 100 determines an error correcting mode. In other words, the error monitoring device 100 may determine an error correcting mode based on the error correction signal received in the operation 575. In other words, as described above in the operation 515, the error monitoring device 100 may not only determine an error correcting mode based on a time point at which the error event occurred, but also determine an error correcting mode based on the error correction signal received from the medical data providing device 200.

In an operation 585, the error monitoring device 100 processes the error event in the determined error correcting mode.

Figure 6:
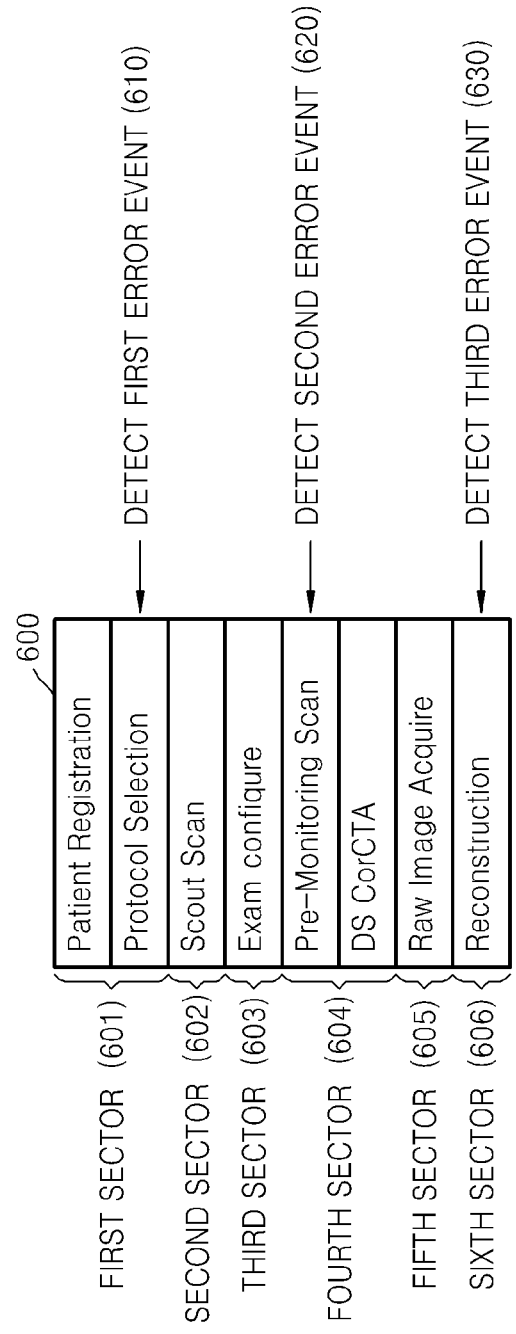
FIG. 6 is a diagram showing a plurality of diagnosis processes according to an exemplary embodiment.

FIG. 6 is a diagram showing a plurality of diagnosis processes according to an exemplary embodiment.

The medical diagnosis device 50 may diagnose a target object via a plurality of diagnosis processes, and a diagnosis process may refer to a series of operations carried out for fulfilling a predetermined objective.

According to the present exemplary embodiment, the medical diagnosis device 50 may diagnose a target object via the 8 diagnosis processes shown in FIG. 6. First, the error monitoring device 100 obtains patient information regarding the target object via the diagnosis process "Patient Registration" and stands by until the target object is located on a diagnosis table. Next, the error monitoring device 100 selects a protocol to be performed with respect to the target object or a sequence of medical signals to be applied to the target object via the diagnosis process "Protocol Selection," and performs a preliminary imaging operation via the diagnosis process "Scout Scan."

Next, the error monitoring device 100 selects parameters for an imaging operation via the diagnosis process "Exam Configure," and, if a contrast agent is injected, a result of the injection of the contrast agent may be confirmed via the diagnosis process "Pre-Monitoring Scan." Next, the error monitoring device 100 images the target object via the diagnosis process "DS CorCTA," obtains video data via the diagnosis process "Raw Image Acquire," and may generate a final medical image via the diagnosis process "Reconstruction."

The plurality of diagnosis processes stated above are merely examples provided for convenience of explanation, and the medical diagnosis device 50 may diagnose a target object by sequentially performing different numbers and different types of diagnosis processes.

The plurality of diagnosis processes stated above may be divided into 6 sectors as shown in FIG. 6. In other words, when error events occur in the respective operations, importance of a diagnosis process may be determined based on significance of effects to a target object, and each sector may include diagnosis processes having equal level of importance.

For example, the diagnosis process "Patient Registration" and the diagnosis process "Protocol Selection" included in a first sector 601 have little effects to a target object even if an error event occurs while the diagnosis processes are being performed. On the contrary, the diagnosis process "Scout Scan" included in a second sector 602 and the diagnosis process "Pre-Monitoring Scan" and the diagnosis process "DS CorCTA" included in a fourth sector 604 are diagnosis processes for directly imaging a target object. Therefore, the diagnosis process "Scout Scan," the diagnosis process "Pre-Monitoring Scan," and the diagnosis process "DS CorCTA" may affect the target object more seriously. Similarly, diagnosis processes in a third sector 603, diagnosis processes in a fifth sector 605, and diagnosis processes in a sixth sector 606 may have different importance than those in the first sector 601, the second sector 602, and the fourth sector 604.

Therefore, the error monitoring device 100 may determine an error correcting mode based on a sector of the overall diagnosis processes to which the diagnosis process corresponding to the error event belongs. In other words, if a first error event 610 occurs at the diagnosis process "Protocol Selection," the diagnosis process at which the first error event 610 occurred belongs to the first sector 601, and thus the error monitoring device 100 may determine the first mode and the second mode as the error correcting mode. In other words, the error monitoring device 100 may restart the diagnosis process "Protocol Selection" at which the first error event 610 is detected (the first mode) and inform about occurrence of the error event to other components of the medical diagnosis device 50 (the second mode).

Furthermore, if a second error event 620 occurs at the diagnosis process "Pre-Monitoring Scan," the diagnosis process "Pre-Monitoring Scan" belongs to the fourth sector 604. Therefore, the error monitoring device 100 may determine the second mode and the third mode as the error correcting mode. In other words, the error monitoring device 100 may inform about occurrence of the error event to other components of the medical diagnosis device 50 (the second mode) and stop operation of the medical diagnosis device 50 (the third mode).

In the same regard, if a third error event 630 occurs at the diagnosis process "Reconstruction," the diagnosis process "Reconstruction" belongs to the sixth sector 606. The error monitoring device 100 may determine a sector to which a diagnosis process corresponding to the third error event 630 and determine the first mode as the error correcting mode. The error monitoring device 100 may process the error event by restarting the diagnosis process "Reconstruction" (the first mode) in the first mode.

Furthermore, the error monitoring device 100 may transmit information indicating occurrence of an error event to the medical data managing device 70 according to the exemplary embodiments described above, and thus the medical data managing device 70 may collect medical data and transmit the medical data to the medical data providing device 200.

Figure 7:
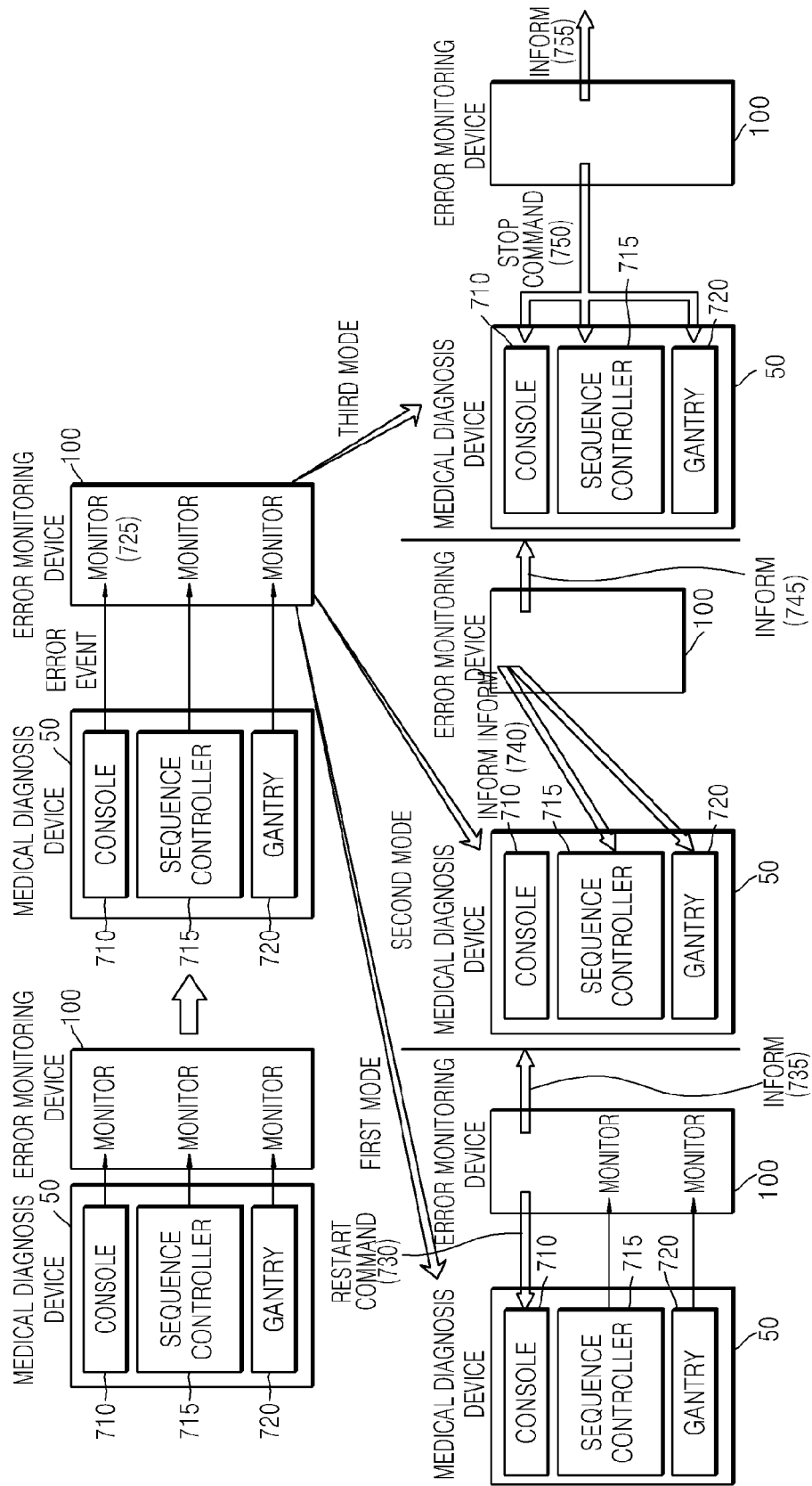
FIG. 7 is a diagram showing that the error monitoring device processes an error event in an error correcting mode, according to an exemplary embodiment.

FIG. 7 is a diagram showing that the error monitoring device 100 processes an error event in an error correcting mode, according to an exemplary embodiment. FIG. 7 shows respective cases regarding the first mode, the second mode, and the third mode.

First, at the upper-left portion of FIG. 7, the error monitoring device 100 monitors the medical diagnosis device 50 and detects occurrence of an error event. In other words, the error monitoring device 100 may detect occurrence of an error event by periodically receiving signals from a console unit 710, a sequence controller 715, and a gantry 720, which are components included in the medical diagnosis device 50.

Next, at the upper-right portion of FIG. 7, the error monitoring device 100 detects an error event occurring at the console unit 710 from among the components of the medical diagnosis device 50. In other words, the console unit 710 transmits a signal indicating occurrence of an error event to the error monitoring device 100, and the error monitoring device 100 receives the signal indicating occurrence of the error event. The error monitoring device 100 determines a diagnosis process corresponding to a time point at which the error event occurred at the console unit 710 and may determine an error correcting mode based on a sector to which the diagnosis process corresponding to the error event belongs.

If the first mode is determined as the error correcting mode (the lower-left portion of FIG. 7), the error monitoring device 100 orders the console unit 710, at which the error event occurred, to restart the correspond diagnosis process (an operation 730). Next, the error monitoring device 100 may inform about the occurrence of the error event to the medical data managing device 70 (an operation 735).

If the second mode is determined as the error correcting mode (the lower-middle portion of FIG. 7), the error monitoring device 100 informs about the error event to components other than the console unit 710 at which the error event occurred, that is, the sequence controller 715 and the gantry 720 (an operation 740). In other words, the error monitoring device 100 may inform the occurrence of the error event at the console unit 710 and a particular diagnosis process corresponding to the error event. In the same regard, the error monitoring device 100 may inform about the occurrence of the error event to the medical data managing device 70 (an operation 745).

If the third mode is determined as the error correcting mode (the lower-right portion of FIG. 7), because the error event seriously affects diagnosis of a target object, the error monitoring device 100 orders the medical diagnosis device 50 to stop operations of all of the components (an operation 750). Next, the error monitoring device 100 may inform about the occurrence of the error event to the medical data managing device 70 (an operation 755).

According to another exemplary embodiment, if an error event is processed under the control of the error monitoring device 100, the error monitoring device 100 may receive signals indicating the resolution of the error event from the respective components of the medical diagnosis device 50.

According to error monitoring apparatuses and error event processing methods according to the exemplary embodiments described above, error events occurring at a medical diagnosis device may be efficiently processed. Furthermore, the error monitoring apparatuses and the error event processing methods according to the exemplary embodiments described above may not only help ex post facto processes of error events, but also immediately process error events. Therefore, the medical diagnosis device 50 may be managed more conveniently.

Figure 8:
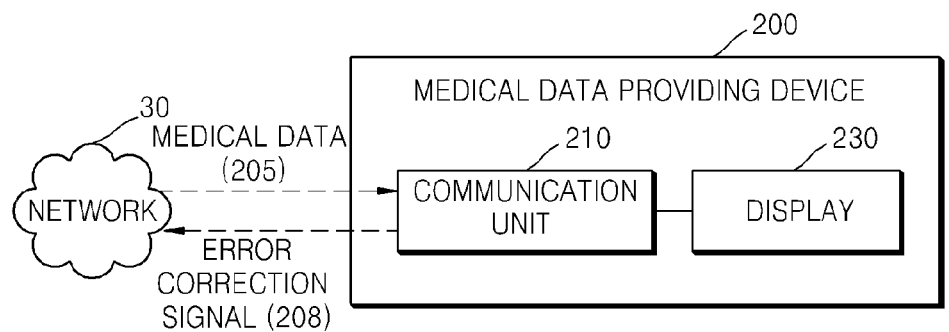
FIG. 8 is a block diagram showing the configuration of a medical data providing device according to an exemplary embodiment.

FIG. 8 is a block diagram showing the configuration of the medical data providing device 200 according to an exemplary embodiment. The medical data providing device 200 according to an exemplary embodiment may include a communication unit 210 and a display 230. However, one or more exemplary embodiments is not limited thereto, and the medical data providing device 200 may include more components or fewer components than the above-stated components.

The communication unit 210 is connected to the network 30 and communicates with an external device or a server. The communication unit 210 may exchange data with a hospital server connected via a picture archiving and communication system (PACS), an external server, the medical diagnosis device 50, the medical data managing device 70, and the medical data providing device 200. Furthermore, the communication unit 210 may perform data communication according to the digital imaging and communication in medicine (DICOM) standard or the TCP/IP protocol.

The communication unit 210 of the medical data providing device 200 may have similar components as those of the communication unit 170 of the error monitoring device 100 and may have a similar structure as that of the communication unit 170 of the error monitoring device 100. Descriptions of components identical to those shown in FIG. 3 will be omitted below.

The communication unit 210 may receive medical data 205 via the network 30. In other words, the communication unit 210 may receive medical data 205 related to an error event from the medical data managing device 70. The exemplary embodiment regarding the medical data 205 described above with reference to FIG. 1 may be applied to the medical data received by the communication unit 210. In other words, the communication unit 210 may receive medical data regarding predetermined periods of time before and after a time point at which the error event occurred. Furthermore, the communication unit 210 may transmit an error correction signal 208 regarding an error event to the medical data managing device 70 or the error monitoring device 100.

The display 230 displays information and data processed by the medical data providing device 200. The display 230 may display various information using text data and graphic data or via a graphic user interface (GUI).

For example, the display 230 may display information regarding a diagnosis process in a screen image and may display log data or video data in a screen image. The display 230 may display log data using text data and display video data using graphic data.

The display 230 may include at least one from among a liquid crystal display (LCD), a thin film transistor LCD, an organic light emitting diode, a flexible display, a 3D display, and an electrophoretic display. Furthermore, the medical data providing device 200 may include two or more displays 230 according to exemplary embodiments.

Furthermore, the display 230 may form a layered structure with a touch pad (e.g., electrostatic capacitive type, pressure resistive type, infrared ray sensitive type, surface acoustic wave type, integral tension measuring type, piezo-effect type, etc.) and be embodied as a touch screen. The display 230 embodied as a touch screen may detect not only a real touch, but also a proximity touch, and may also detect touch inputs (e.g., touch and hold, tap, double-tap, flick, etc.) to information displayed by the display 230. Furthermore, the display 230 may detect a drag input from a point at which the initial touch is detected or a multi-touch input (pinch and unpinch) to two or more points. For example, the display 230 may receive a user input for selecting some of a plurality of diagnosis processes.

According to another exemplary embodiment, the medical data providing device 200 according to an exemplary embodiment may further include an acoustic output unit. The acoustic output unit may acoustically output voice data in the medical data received by the medical data providing device 200.

Hereinafter, a method of providing medical information using components included in the medical data providing device 200 will be described with reference to FIG. 9. The flowchart shown in FIG. 9 includes operations that are chronologically carried out by the medical data providing device 200, the communication unit 170, and the display 230 shown in FIG. 8. Therefore, even if omitted below, any of descriptions given above in relation to the components shown in FIG. 8 also apply to the flowcharts shown in FIG. 9.

Figure 9:
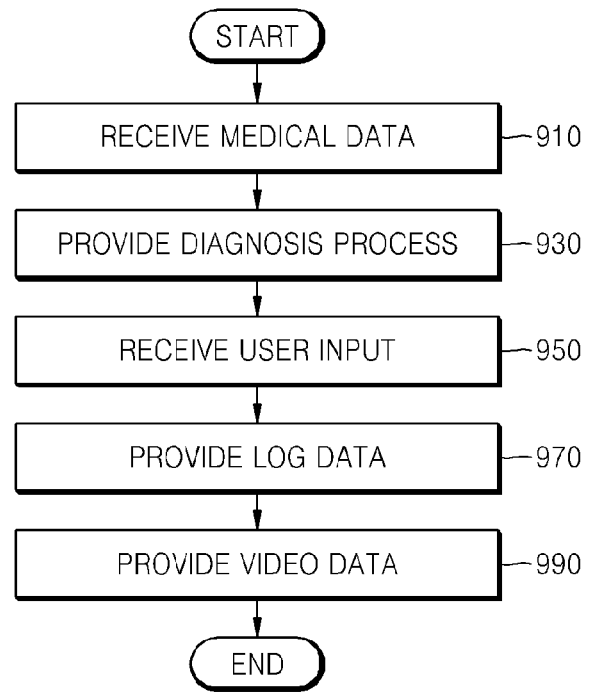
FIG. 9 is a flowchart showing a method of providing medical information according to an exemplary embodiment.

FIG. 9 is a flowchart showing a method of providing medical information according to an exemplary embodiment.

In an operation 910, the medical data providing device 200 receives medical data. The medical data providing device 200 may receive medical data including log data and video data from the medical data managing device 70, where the medical data may include data related to an error event occurred at the medical diagnosis device 50.

Furthermore, as described above, medical data received by the medical data providing device 200 may be medical data regarding predetermined periods of time before and after a time point at which the error event occurred.

In an operation 930, the medical data providing device 200 provides information regarding diagnosis processes in a screen image. In other words, the medical data providing device 200 may display information regarding one or more diagnosis processes related to the medical data at a portion of a screen image.

For example, the medical data providing device 200 may assort and display information regarding all of diagnosis processes of the medical diagnosis device 50 including a diagnosis process at which the error event occurred. The medical data providing device 200 according to an exemplary embodiment may assort a plurality of diagnosis processes in the order the diagnosis processes are carried out and provide a list of the assorted diagnosis processes to a user.

In an operation 950, the medical data providing device 200 receives a user input for selecting one from among a plurality of diagnosis processes. In other words, the medical data providing device 200 may detect a user input for selecting a region corresponding to one from among the plurality of diagnosis processes provided in the operation 930. For example, the medical data providing device 200 may detect a touch input of a user for selecting one from among diagnosis processes displayed in a screen image.

In an operation 970, the medical data providing device 200 provides log data in a screen image. In other words, the medical data providing device 200 may extract log data corresponding to a diagnosis process selected by the user input received in the operation 950 from log data included in the medical data and display the extracted log data. In other words, the medical data providing device 200 may provide a portion of log data selected by the user from the entire log data to the user.

The medical data providing device 200 may provide log data at a portion of a screen image, and the medical data providing device 200 may display log data in a region different from the region in which the diagnosis processes are displayed in the operation 930.

In an operation 990, the medical data providing device 200 provides video data in a screen image. In other words, the medical data providing device 200 may extract video data corresponding to a diagnosis process selected by the user input received in the operation 950 from video data included in the medical data and display the extracted video data. Similar to the operation 970, the medical data providing device 200 may provide a portion of video data selected by the user from the entire video data to the user.

For example, if video data includes moving pictures, the medical data providing device 200 may display video data corresponding to a period of time corresponding to a diagnosis process selected by the user.

The medical data providing device 200 may provide video data at a portion of a screen image, and the medical data providing device 200 may display video data in a region different from the regions in which the diagnosis processes and log data are displayed in the operation 930 and the operation 970.

The medical data providing device 200 according to an exemplary embodiment may synchronize the log data output in the operation 970 and the video data output in the operation 990 and display the synchronized data. In other words, because medical data of the operations 970 and 990 correspond to the same diagnosis process selected by the user, the medical data providing device 200 may synchronize the log data and the video data with respect to time and display the synchronized data in a screen image. Detailed descriptions thereof will be given below with reference to FIG. 11.

Figure 10:
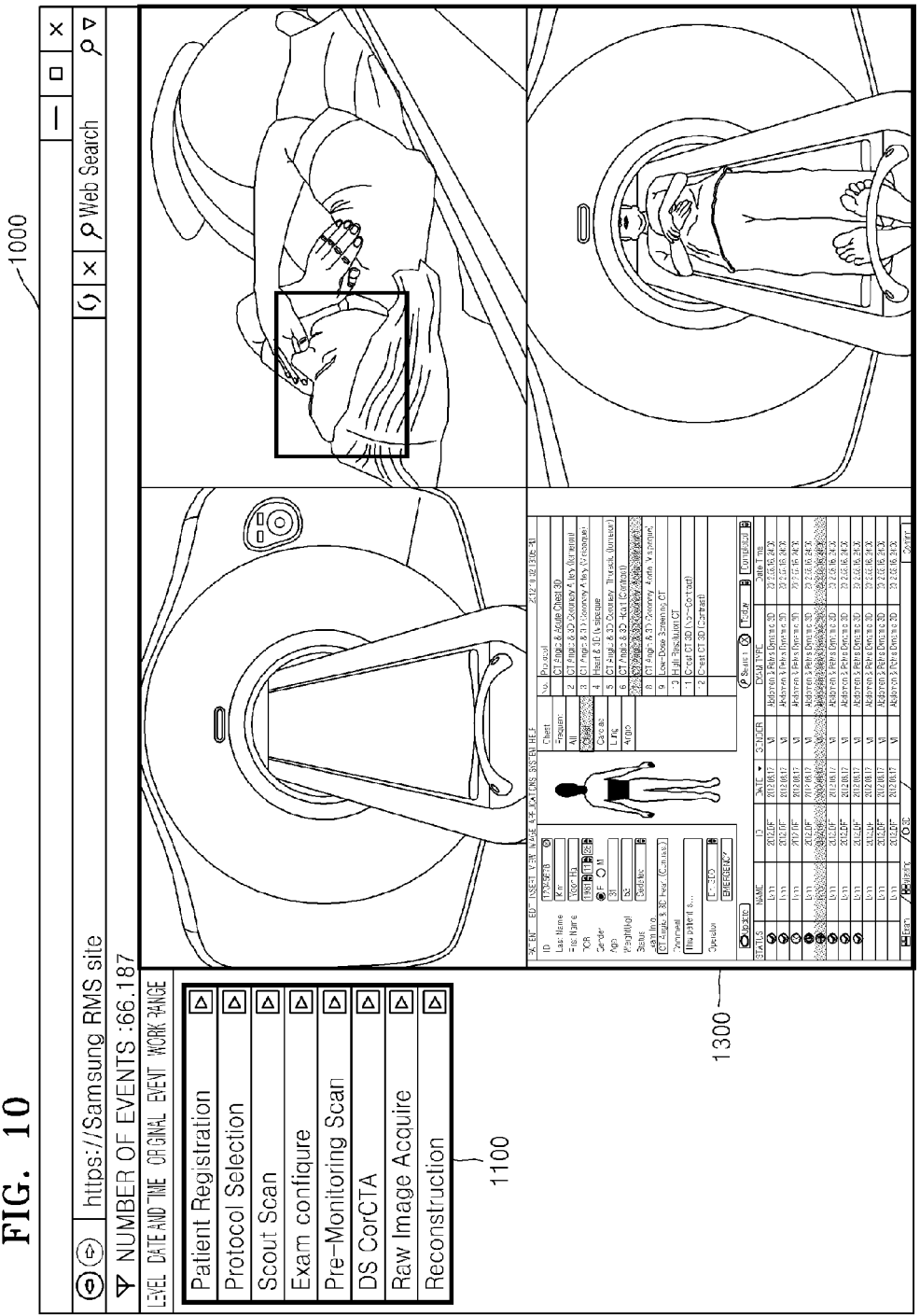
FIG. 10 is a diagram showing an example of providing medical information in a screen image, according to an exemplary embodiment.

FIG. 10 is a diagram showing an example of providing medical information in a screen image, according to an exemplary embodiment.

The medical data providing device 200 may provide medical information and medical data in a screen image 1000. In other words, as shown in FIG. 10, the medical data providing device 200 displays information regarding a plurality of diagnosis processes at first region 1100 of the screen image 1000. The medical data providing device 200 according to an exemplary embodiment may assort the plurality of diagnosis processes in the order the plurality of diagnosis processes are to be carried out and display the assorted diagnosis processes at the first region 1100.

Next, the medical data providing device 200 may provide medical data at a region of the first region 1100 different from the first region 1100. In FIG. 10, the medical data providing device 200 displays video data from the medical data in a third region 1300 of the screen image 1000. The term "third region 1300" is used for convenience of explanation regarding FIGS. 10 and 11, and detailed descriptions of a "second region" will be given below with reference to FIG. 11.

The medical data providing device 200 may display various types of video data in a screen image. For example, the medical data providing device 200 may display various visually recognizable data including data obtained by capturing an image nearby a gantry of the medical diagnosis device 50, data obtained by capturing an image of a console unit or a user input unit of the medical diagnosis device 50, data obtained by recording screen images output to the console unit of the medical diagnosis device 50, data obtained by capturing an image of a target object located at the gantry, data obtained by capturing an image inside a shielded room, and medical image data that is a result of diagnosis regarding the target object.

The medical data providing device 200 may divide the third region 1300 of a screen image into a plurality of sub-regions and may display different types of video data in the respective sub-regions. In other words, as shown in FIG. 10, the medical data providing device 200 may divide the third region 1300 into 4 sub-regions and may display video data showing a gantry, video data showing a target object, video data showing recorded screen images of the console unit, and video data showing the interior of a shielded room in the respective sub-regions. Video data displayed in the respective sub-regions may be data synchronized with respect to time and generated with respect to a same time point or a same period of time.

Figure 11:
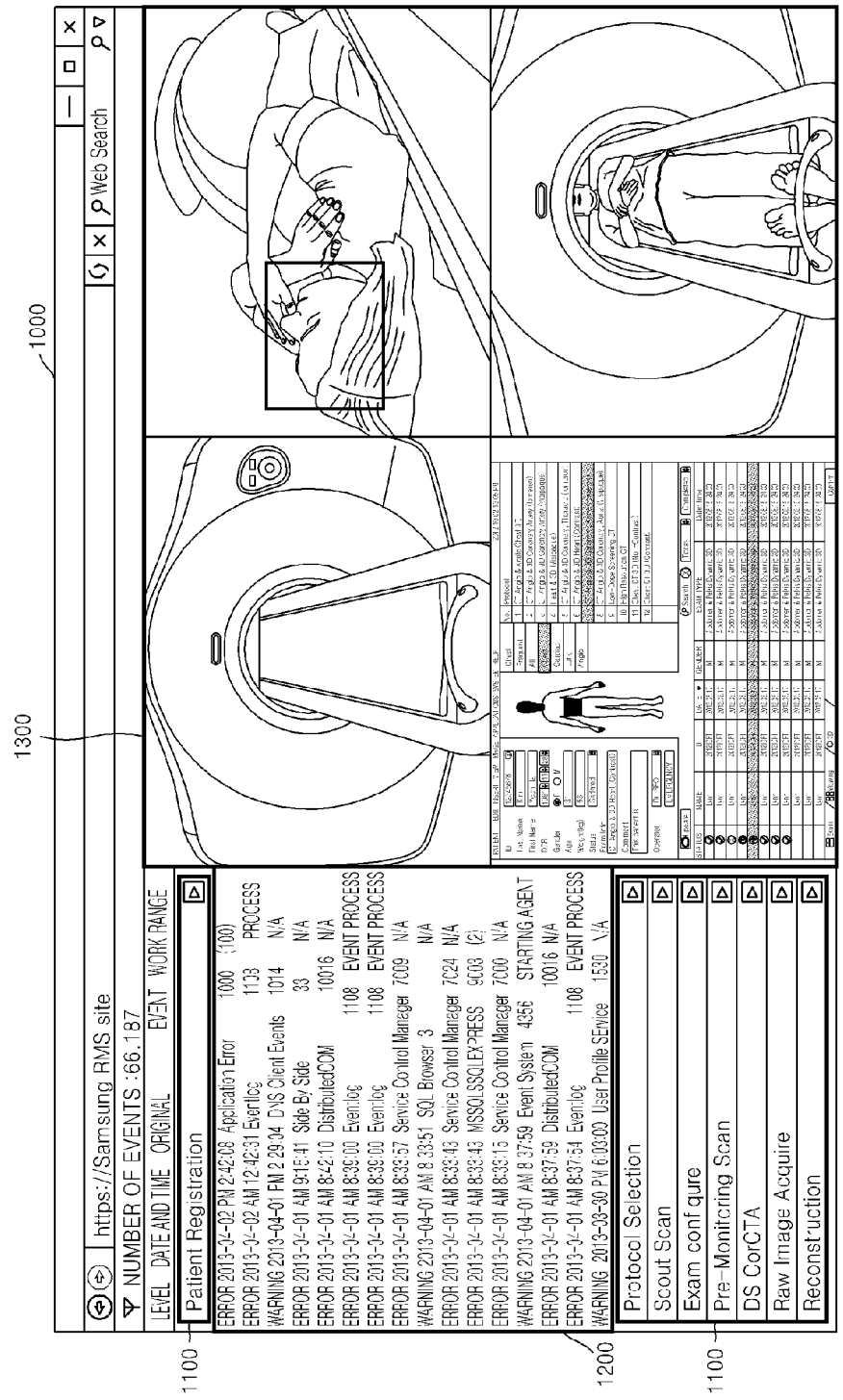
FIG. 11 is a diagram showing an example of providing medical information in a screen image, according to another exemplary embodiment.

FIG. 11 is a diagram showing an example of providing medical information in a screen image, according to another exemplary embodiment.

The medical data providing device 200 may provide log data in the screen image 1000. In other words, as described above with reference to FIG. 10, the medical data providing device 200 may display information regarding a diagnosis process in the first region 1100 and display video data in the third region 1300. Furthermore, the medical data providing device 200 may display log data in a second region 1200, which is a portion of the screen image 1000.

Log data displayed at the second region 1200 and video data displayed at the third region 1300 that are provided by the medical data providing device 200 may be data corresponding to a diagnosis process selected by a user from among a plurality of diagnosis processes. For example, the medical data providing device 200 may receive a user input for selecting the diagnosis process "Patient Registration" from among a plurality of diagnosis processes displayed at the first region 1100 in FIG. 10. Next, the medical data providing device 200 may display log data and video data corresponding to the diagnosis process "Patient Registration" selected by the user at the second region 1200 and the third region 1300, respectively.

When the medical data providing device 200 provides medical data based on a user selection, the medical data providing device 200 may select a region adjacent to a region at which a diagnosis process selected by the user is displayed as the second region 1200. In other words, as shown in FIG. 11, the medical data providing device 200 may set a region having a predetermined size and being adjacent to a portion of the first region 1100 of FIG. 10 at which the diagnosis process "Patient Registration" is displayed as the second region 1200 and output log data at the second region 1200. At the same time, the medical data providing device 200 may move the remaining of the first region 1100 other than the portion corresponding to the diagnosis process "Patient Registration" downward by the size of the second region 1200.

Locations, sizes, and arrangements of the first region 1100, the second region 1200, and the third region 1300 stated above are merely examples, and one or more exemplary embodiments is not limited thereto. In other words, according to an exemplary embodiment other than the exemplary embodiments described above, the medical data providing device 200 may set an empty region adjacent to the bottom of the first region 1100 of FIG. 10 as the second region 1200 and output log data at the second region 1200.

The medical data providing device 200 according to an exemplary embodiment may synchronize log data and video data. In other words, based on a user input for selecting the diagnosis process "Patient Registration," the medical data providing device 200 may extract portions of data related to the diagnosis process "Patient Registration" from the entire log data and the entire video data.

Next, the medical data providing device 200 may display extracted log data and extracted video data in the screen image 1000. Here, the log data and the video data corresponding to the same diagnosis process "Patient Registration," and may correspond to a same time point and a same time slot. In the exemplary embodiment shown in FIG. 11, the diagnosis process "Patient Registration" is performed in a time slot from '6:03:00 PM on 2013.03.30' to '2:41:08 PM on 2013.04.02.' Therefore, the medical data providing device 200 extracts log data corresponding to the corresponding time slot from medical data and displays the extracted log data in a second region 1200 in the screen image 1000. At the same time, the medical data providing device 200 extracts video data corresponding to the same time slot and may display the extracted video data in a third region 1300 in the screen image 1000.

Furthermore, the medical data providing device 200 according to an exemplary embodiment may receive a user input for selecting a portion of log data to be displayed in the second region 1200 and may display video data corresponding to the same time point, at which the selected log data is generated, in the third region 1300.

Furthermore, the medical data providing device 200 may output voice data from medical data. In other words, the medical data providing device 200 may output voice data that is time-synchronized with log data and video data.

Figure 12:
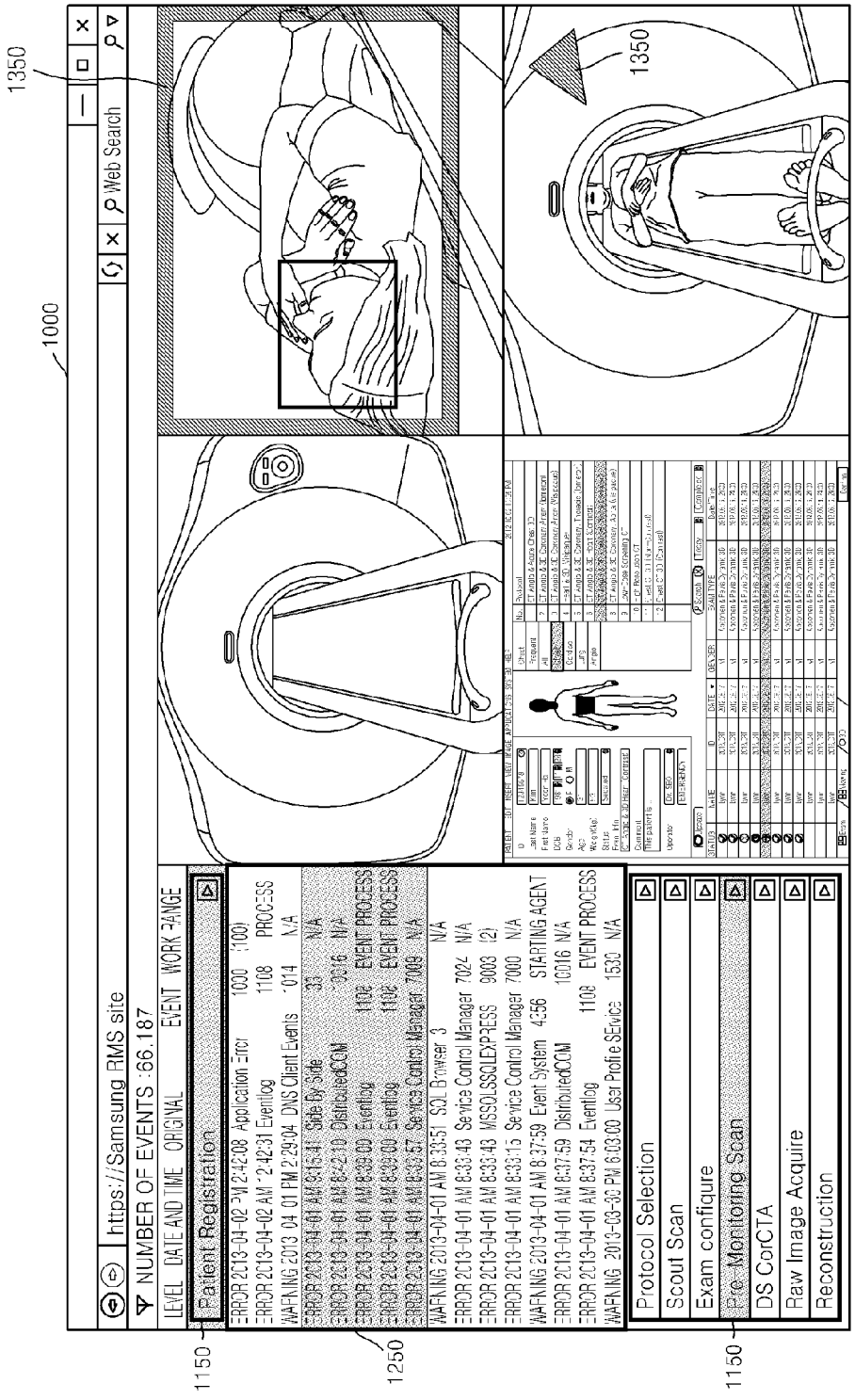
FIG. 12 is a diagram showing an example of providing medical information in a screen image, according to another exemplary embodiment.

FIG. 12 is a diagram showing an example of providing medical information in a screen image, according to another exemplary embodiment.

In addition to the exemplary embodiment shown in FIG. 11, the medical data providing device 200 may display visually distinguishable data corresponding to time points at which errors occurred in medical data. The medical data providing device 200 according to an exemplary embodiment may display occurrence of an error event by using various visual effects, such as changing at least one from among brightness, contrast, or color of a region corresponding to a portion of data corresponding to the error event, displaying a marker at the region, or indicating the region with a thick borderline.

In the exemplary embodiment shown in FIG. 12, the medical data providing device 200 may change or invert colors of the diagnosis process "Patient Registration" and the diagnosis process "Pre-Monitoring Scan," at which error events occurred, in the first region 1100. Therefore, a user of the medical data providing device 200 may instantly determine in which of the entire diagnosis processes an error event occurred.

Furthermore, the medical data providing device 200 may apply visual effects to a part of the log data displayed in the second region 1200 corresponding to a time slot at which an error occurred, so that the part of the log data may be distinguished from the other part of the log data (operation 1250).

In the same regard, the medical data providing device 200 may display thick borders or display a an error-indicating marker with respect to video data displayed in the third region 1300 (operation 1350), thereby indicating that the video data being displayed is data corresponding to a time slot at which an error occurred.

Other than the above exemplary embodiments, the medical data providing device 200 may actively inform occurrence of an error event to a user by applying various types of visual effects in various ways.

If the medical data providing device 200 outputs voice data, the medical data providing device 200 may inform occurrence of an error event by outputting a beep, an alarm sound, or a warning sound. In other words, the medical data providing device 200 may inform a user by outputting pre-stored sound data a designated period of time before a time point at which an error occurred.

According to the above exemplary embodiments, a user may recognize system log of a medical diagnosis system, video data, and voice data together during analysis of an error event. Therefore, the user may quickly and efficiently perform a debugging process for resolving the error event and may efficiently manage the medical diagnosis system.

In addition, other exemplary embodiments can also be implemented through computer readable code/instructions in/on a medium, e.g., a computer readable medium, to control at least one processing element to implement any above described exemplary embodiment. The medium can correspond to any medium/media permitting the storage and/or transmission of the computer readable code.

The computer readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer readable code is stored/transferred and executed in a distributed fashion. Furthermore, the processing element could include a processor or a computer processor, and processing elements may be distributed and/or included in a single device.

While exemplary embodiments have been described with respect to a limited number of embodiments, those skilled in the art, having the benefit of this disclosure, will appreciate that other embodiments can be devised which do not depart from the scope as disclosed herein. Accordingly, the scope should be limited only by the attached claims.

What is claimed is:

1. A method for processing an error event using an error monitoring device, the method comprising:
   detecting an error event at a medical diagnosis system;
   determining an error correcting mode from among a first mode for restarting a diagnosis process at which the error event occurred, a second mode for informing the error event to components of the medical diagnosis system at which the error event did not occur, and a third mode for stopping operation of the medical diagnosis system, based on information regarding the error event; and
   processing the error event based on the determined error correcting mode.

2. The method of claim 1, wherein the detecting of the error event comprises receiving information regarding the diagnosis process at which the error event occurred.

3. The method of claim 2, wherein, in the second mode, information regarding the diagnosis process is transmitted to components at which the error event did not occur.

4. The method of claim 1, wherein the determining of the error correcting mode comprises determining the error correcting mode based on a time point at which the error event is detected.

5. The method of claim 4, wherein the determining of the error correcting mode further comprises determining the error correcting mode based on a sector of the overall diagnosis processes that corresponds to the diagnosis process at which the error event occurred.

6. The method of claim 1, further comprising transmitting the error event to a medical data managing device.

7. The method of claim 6, wherein the determining of the error correcting mode comprises:
   determining the error correcting mode based on an error correcting signal received from a medical data providing device,
   wherein the medical data managing device informs the medical data providing device of the error event.

8. A computer readable recording medium having recorded thereon a computer program for implementing the method of claim 1.

9. An error monitoring device configured to process an error event, the error monitoring device comprising:
   an error detector configured to detect an error event at a medical diagnosis system;
   a mode determiner configured to determine an error correcting mode from among a first mode for restarting a diagnosis process at which the error event occurred, a second mode for informing the error event to components of the medical diagnosis system at which the error event did not occur, and a third mode for stopping operation of the medical diagnosis system, based on information regarding the error event; and
   an error resolving unit configured to process the error event based on the determined error correcting mode.

10. The error monitoring device of claim 9, wherein the error detector is further configured to receive information regarding the diagnosis process at which the error event occurred.

11. The error monitoring device of claim 10, wherein, in the second mode, information regarding the diagnosis process is transmitted to components at which the error event did not occur.

12. The error monitoring device of claim 9, wherein the mode determiner is further configured to determine the error correcting mode based on a time point at which the error event is detected.

13. The error monitoring device of claim 12, wherein the mode determiner is further configured to determine the error correcting mode based on a sector of the overall diagnosis processes that corresponds to the diagnosis process at which the error event occurred.

14. The error monitoring device of claim 9, further comprising a communication unit configured to transmit the error event to a medical data managing device.

15. The error monitoring device of claim 14,
   wherein the mode determiner is further configured to determine the error correcting mode based on an error correcting signal received from a medical data providing device, and
   wherein the medical data managing device is configured to inform the medical data providing device of the error event.

16. A method for providing medical information using a medical data providing device, the method comprising:
   receiving medical data from a medical data managing device;
   providing a diagnosis process related to the medical data at a first region of a screen image;
   providing log data from the medical data that corresponds to the diagnosis process at a second region of the screen image based on a user input for selecting the diagnosis process from among a plurality of diagnosis processes; and providing video data from the medical data that corresponds to the selected diagnosis process at a third region of the screen image.

17. The method of claim 16, wherein the medical data relates to an error event at a medical diagnosis system.

18. The method of claim 17, wherein the medical data relates to predetermined periods of time before and after a time point at which the error event occurred.

19. The method of claim 17, wherein the providing of the diagnosis process comprises displaying the diagnosis process at which the error event is detected to be visually distinguishable.

20. The method of claim 17 wherein the providing of the log data comprises displaying log data corresponding to the detection of the error event to be visually distinguishable.

21. The method of claim 17, wherein the providing of the video data comprises displaying video data corresponding to the detection of the error event to be visually distinguishable.

22. The method of claim 16, wherein the log data provided at the second region and the video data provided at the third region are synchronized with each other.

23. The method of claim 16, wherein the providing of the diagnosis process comprises assorting and displaying a plurality of diagnosis processes in an order in which the plurality of diagnosis processes are carried out.

24. The method of claim 16, wherein the second region is adjacent to the first region at which the selected diagnosis process is displayed.

25. The method of claim 16, wherein the video data comprises at least one of video data showing a gantry, video data showing a user input unit, video data showing recorded screen images of a console unit, video data showing a target object, video data showing an interior of a shielded room, and video data showing diagnosis of the target object.

26. The method of claim 16, wherein the medical data further comprises voice data.

27. A computer readable recording medium having recorded thereon a computer program for implementing the method of claim 16.

28. A medical data providing device for providing medical data, the medical data managing device comprising:
   a communication unit configured to receive medical data from a medical data managing device; and
   a display configured to provide a diagnosis process related to the medical data at a first region of a screen image, provide log data from the medical data that corresponds to the diagnosis process at a second region of the screen image based on a user input for selecting the diagnosis process from among a plurality of diagnosis processes, and providing video data from the medical data that corresponds to the selected diagnosis process at a third region of the screen image.

29. The medical data providing device of claim 28, wherein the medical data relates to an error event at a medical diagnosis system.

30. The medical data providing device of claim 29, wherein the medical data relates to predetermined periods of time before and after a time point at which the error event occurred.

31. The medical data providing device of claim 29, wherein the display is further configured to display the diagnosis process at which the error event is detected to be visually distinguishable.

32. The medical data providing device of claim 29, wherein the display is further configured to display log data corresponding to the detection of the error event to be visually distinguishable.

33. The medical data providing device of claim 29, wherein the display is further configured to display video data corresponding to the detection of the error event to be visually distinguishable.

34. The medical data providing device of claim 28, wherein the log data provided at the second region and the video data provided at the third region are synchronized with each other.

35. The medical data providing device of claim 28, wherein the display is further configured to assort and display a plurality of diagnosis processes in an order in which the plurality of diagnosis processes are carried out.

36. The medical data providing device of claim 28, wherein the second region is adjacent to the first region at which the selected diagnosis process is displayed.

37. The medical data providing device of claim 28, wherein the video data comprises at least one of video data showing a gantry, video data showing a user input unit, video data showing recorded screen images of a console unit, video data showing a target object, video data showing an interior of a shielded room, and video data showing diagnosis of the target object.

38. The medical data providing device of claim 28, wherein the medical data further comprises voice data.

39. A method for processing and displaying an error event using a medical diagnosis system, the method comprising:
   detecting, at an error monitoring device, an error event at a medical diagnosis device;
   determining, at the error monitoring device using error event information corresponding to the error event, an error correcting mode from among a first mode for restarting a diagnosis process where the error event occurred, a second mode for informing components where the error event did not occur, and a third mode for stopping operation;
   processing, at the error monitoring device, the error event based on the error correcting mode;
   transmitting the error event information to a medical data managing device;
   receiving, at a medical data providing device, medical data from the medical data managing device including the error event information;
   providing the diagnosis process related to the medical data at a first region of a screen, log data from the medical data at a second region of the screen, and video data from the medical data at a third region of the screen.

* * * * *